United States Patent [19]
McGuire

[11] Patent Number: 5,683,400
[45] Date of Patent: Nov. 4, 1997

[54] GRAFT PREPARATION TABLE

[76] Inventor: David A. McGuire, 3418 Lakeside Dr., Anchorage, Ak. 99515

[21] Appl. No.: 477,379

[22] Filed: Jun. 7, 1995

Related U.S. Application Data

[63] Continuation-in-part of Ser. No. 347,578, Nov. 30, 1994, abandoned, which is a continuation-in-part of Ser. No. 180,956, Jan. 13, 1994, Pat. No. 5,562,669, which is a continuation-in-part of Ser. No. 956,733, Oct. 2, 1992, Pat. No. 5,391,170, which is a continuation-in-part of Ser. No. 806,906, Dec. 13, 1991, Pat. No. 5,257,996, and a continuation-in-part of Ser. No. 839,466, Feb. 19, 1992, Pat. No. 5,520,693.

[51] Int. Cl.$^6$ ............................................. A61B 17/58
[52] U.S. Cl. ........................... 606/96; 606/86; 606/104; 606/87; 606/88
[58] Field of Search ............................ 606/86, 87, 88, 606/96, 97, 98, 104; 623/13

[56] References Cited

U.S. PATENT DOCUMENTS

| | | | |
|---|---|---|---|
| 4,421,112 | 12/1983 | Mains | 606/96 |
| 4,585,458 | 4/1986 | Kurland | 623/13 |
| 4,828,562 | 5/1989 | Kenna | 623/13 |
| 5,254,119 | 10/1993 | Schreiber | 606/96 |
| 5,257,996 | 11/1993 | McGuire | 606/104 |
| 5,320,115 | 6/1994 | Kenna | 128/898 |
| 5,366,457 | 11/1994 | McGuire et al. | 606/86 |

FOREIGN PATENT DOCUMENTS

0495487A2  7/1992  European Pat. Off. .

*Primary Examiner*—Michael A. Brown
*Attorney, Agent, or Firm*—Bromberg & Sunstein LLP

[57] ABSTRACT

A graft preparation table including a bone block drill guide and a suturing station. The bone block drill guide has a central tunnel and first and second parallel tunnels intersecting opposite sides of the central tunnel and parallel to the central tunnel. A bone plug is longitudinally inserted into the central column so that parallel grooves may be formed in the bone plug by drilling through the first and second parallel tunnels. The suturing station includes a tensioning track and a pair of suture blocks separated along the track. Each suture block includes a chamber for accommodating a bone plug and suture openings on opposite sides of the suture block. The distance between the suture blocks on the tensioning track may be adjusted to achieve the desired tension on the ligament replacement looped about the bone plugs. A stop pin is inserted into each suture block to hold the bone plug in its respective chamber. A needle carrying a suture is inserted through a suturing opening to attach the ligament replacement to the bone plug. The needle pierces the ligament replacement and the bone plug and exits through the suturing opening on the opposite side. Suturing is conducted with the ligament replacement under tension.

20 Claims, 6 Drawing Sheets

GRAFT PREPARATION TABLE

This application is a continuation-in-part of U.S. application Ser. No. 08/347,578, filed Nov. 30, 1994 now abandoned, which is a continuation-in-part of U.S. application Ser. No. 08/180,956, filed Jan. 13, 1994 now U.S. Pat. No. 5,562,669 which is a continuation-in-part of U.S. application Ser. No. 07/956,733 filed Oct. 2, 1992, now U.S. Pat. No. 5,391,170 which is a continuation-in-part of U.S. applications Ser. No. 806,906, filed Dec. 13, 1991 (now issued as U.S. Pat. No. 5,257,996 on Nov. 2, 1993), and a CIP of Ser. No. 07/839,466 filed Feb. 19, 1992, now U.S. Pat. No. 5,520,693. These applications and patents, which all relate to cruciate ligament reconstruction, are hereby incorporated by reference herein.

BACKGROUND OF THE INVENTION

The present invention relates to the field of arthroscopic surgery, particularly anterior cruciate ligament reconstruction.

One common approach to cruciate ligament reconstruction is the use of the patellar tendon to form a bone-tendon-bone graft. This involves cutting out a bone block from the top of the patella. Deviations from proper technique for removal of the patellar bone block have resulted in reports of patellar tendinitis, patellar fractures and even, in some instances, ruptures of the patellar ligament after the grafting procedure. Whether or not these complaints are properly related to the use of the patellar bone block in cruciate ligament reconstruction, these concerns are reason enough to identify an alternate method for performing the surgery.

Cruciate ligament reconstruction involves the drilling of a tunnel through the tibia and into the femur. The tunnels are used for insertion of a graft to replace the damaged cruciate ligament. The accuracy in drilling these tunnels is critical to providing a satisfactory repair. A commonly used method of directing a drill to form these tunnels is by using a guide wire drilled through the bone first. The location of the guide wire can be tested before drilling out the tunnel. A cannulated drill is then inserted over the guide wire to drill the full size tunnel. When it has been desirable to retain the core of the bone tunnel being drilled, a coring reamer is used. However, when a coring reamer is used over a guide wire, the guide wire produces a stress riser in the bone core. Moreover, the use of a guide wire is generally inadequate to accurately guide a coring reamer throughout the drilling of an entire bone tunnel.

SUMMARY OF THE INVENTION

The present invention is directed to a graft preparation table including a bone block drill guide and a suturing station. The graft preparation table of the invention advantageously facilitates fast and accurate preparation of a bone-tendon-bone graft.

The bone block drill guide provides a central tunnel for receiving a bone block. First and second parallel tunnels intersect opposite sides of the central tunnel and are parallel to the central tunnel. A bone plug is longitudinally inserted into the central column. A drill is operated through the first and second parallel tunnels to create a groove along opposite sides of the bone plug. The bone block drill guide may include a cap having two holes that align with the first and second parallel tunnels.

After completing the bone plug with opposite parallel grooves, a ligament replacement is sutured to the bone plugs. The ligament replacement may be a semitendinosus tendon and/or gracilis. The graft preparation table includes a suturing station having a tensioning track on which a pair of suture blocks are attached. Each suture block includes a tunnel for receiving the bone plug with a loop of ligament replacement wrapped around along the grooves of the bone plug. Each suture block has suturing openings on opposite sides of the suture block. The suture openings are aligned with one another and with the chamber therebetween. The chamber preferably has a central tunnel and first and second parallel tunnels intersecting opposite sides of the central tunnel and parallel to the central tunnel. A needle inserted through a suturing opening of a suture block can be extended across the first and second tunnels and the central tunnel into the suturing opening on the opposite side to bring a suture through the ligament replacement in the grooves of the bone plug and pierce the bone plug. The suture blocks are held an adjustable distance from one another on the tensioning track. One of the suture blocks may be attached to a ratchet rod having a series of grooves for adjustably engaging ridges fixed to the suturing station. By pulling back on the ratchet rod, the bone suture blocks are pulled from one another increasing tension on the loop of ligament replacement. Tension can be released by axial rotation of the ratchet rod to disengage the grooves from the ridges. Each suture block includes a hole for receiving a stop pin which holds the bone plug within the chamber.

Other objects and advantages of the invention shall become apparent in the following description of the preferred embodiments taken in conjunction with the drawings.

BRIEF DESCRIPTION OF THE DRAWINGS

FIG. 3b is an end view of the broach of FIG. 3a.

FIG. 4b is a side view of the bone plug of FIG. 4a.

FIG. 7b is a plan view of the bone block drill guide of FIG. 7a.

DETAILED DESCRIPTION OF THE PREFERRED EMBODIMENTS

Figure 1:
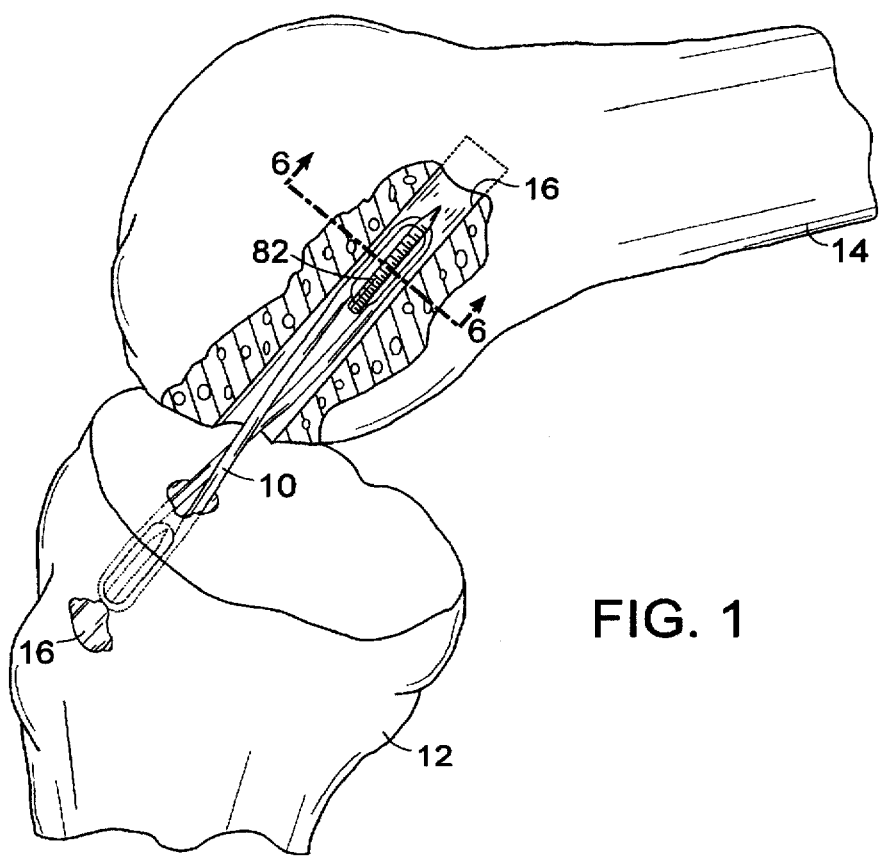
FIG. 1 is a perspective view in partial cross section of a reconstructed ligament formed with the present invention.

Referring now to the drawings, a reconstructed ligament 10 for a knee joint is shown in FIG. 1 in accordance with an embodiment of the present invention. The cruciate ligament reconstruction surgical operation can be conducted as an open surgery, or preferably, through arthroscopic surgery. The arthroscopic surgical method making use of the present invention shall now be described.

Arthroscopic diagnostic procedures are first conducted without tourniquet control in order to allow sufficient time for the ACL reconstruction procedure. Conventional anteromedial and distal lateral portals are drilled to give access to the knee joint for these procedures. The procedures may include meniscotomy, meniscal repair, removal of loose bodies, debridement of anterior cruciate ligament tear, etc. Notchplasty may be commenced under tourniquet control. The boundary of the notchplasty should be sufficiently wide (about 2 cm.) and sufficiently posterior to include the posterior lateral femoral cortex in order to ensure accurate placement and subsequent isometry.

In order to proceed with anterior cruciate ligament reconstruction, a vertical incision is made medial to the tibial tubercle approximately 2.5 cm. in length. The skin incision may be undermined in such a fashion as to provide sufficient mobility for retraction, while harvesting the tibial and femoral bone cores. A carefully placed anteromedial tibial incision may begin approximately 1 cm. medial to the tibial tubercle and 2 cm. distal to the joint line. Conventional surgical procedures are used to excise a semitendinosus tendon, and, if desired, the accompanying gracilis. Alternative ligament replacement materials may be substituted for the semitendinosus tendon and gracilis and used in the composite graft.

The two major bones that meet at the knee joint are the tibia 12 and the femur 14. A bone tunnel 16 is drilled through each of these two bones. The tunnels 16 may be drilled with a regular drill that crushes and removes the bone within the tunnel. However, it is preferable to use a coring reamer to drill the bone tunnels. The reamer drills out a core of bone through each of the bone tunnels. The bone core can then be used to form a bone plug in the composite graft that will be replaced when reconstructing the ligament. In using the coring reamer to drill out a core that may be reused in the composite graft, it is important that a guide pin not be inserted into the core for directing the reamer. The hole formed by the guide pin through the center of the core would form a stress riser in the bone plug making the bone plug subject to fracture. A tibial guide 30 properly orients and guides a coring reamer for making the bone tunnels without a guide wire.

Figure 2:
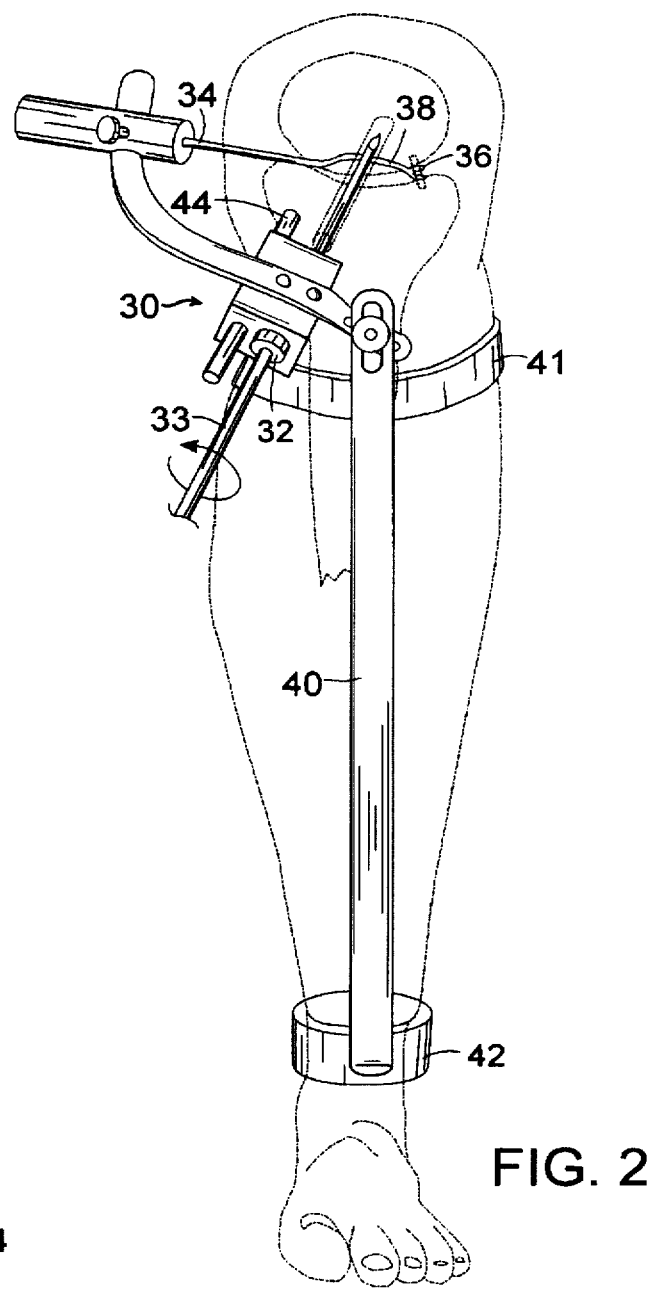
FIG. 2 is an isometric view of a tibial drill guide for use with the present invention.
Figure 9:
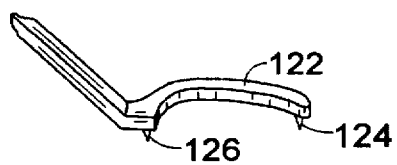
FIG. 9 is an isometric view of the distal end of the positioning arm of the tibial guide of FIG. 8.

Referring now to FIG. 2, the tibial guide 30 is shown. A pipe 32 is oriented at approximately 55° to horizontal. The pipe 32 provides a cylindrical tunnel that serves to guide a coring reamer 33 or other drill inserted therethrough. With the patient's leg held fixed at approximately 110° to 120°, the guide can be used for drilling both the tibial tunnel and then the femoral tunnel. Therefore, a portal for the drill is not required behind the femur and a closed tunnel can be drilled. Both tunnels are drilled through the tibia from the anteromedial tibial incision.

A positioning arm 34 is attached to the pipe 32. The positioning arm 34 has a fork 36 at its far end. The fork 36 has two rounded prongs. The fork 36 is attached to an arcuate portion 38 of the arm 34. The arcuate portion 38 allows for maneuverability of the arm 34 within the knee area upon insertion through the anteromedial portal. Meanwhile, the arthroscope is inserted into the knee joint through the distal lateral portal. The fork 36 needs to be placed against the leading edge of the posterior cruciate ligament. The positioning arm 34 is shaped and oriented with respect to the pipe 32 so that the hole drilled by a reamer or drill through the pipe 32 is directed through the tibia to a point approximately 5 or 6 millimeters from the leading edge of the posterior cruciate ligament. The center of the tibial tunnel is further defined by the tangent to the center of the inner circumference of the anterior one-third of the lateral meniscus.

An adjustable rod 40 is attached to the pipe 32 at one end. A calf strap 41 secures the guide to the patient's leg. The guide has an ankle strap 42 proximate the opposite end of the rod 40. The rod 40 can be adjusted in length to accommodate different leg sizes. The calf strap 41 and ankle strap 42 provide anchors for achieving and maintaining proper orientation of the pipe 32. The straps are affixed with the fork 36 oriented properly around the PCL attachment on the tibia.

Another anchor to securely orient the pipe 32 is provided by a K-wire 44. The K-wire 44 is shot through the skin of the patient's leg and into the tibia. The K-wire 44 may be positioned on the guide 30 closely adjacent the pipe 32 so that the hole formed in the tibia by the K-wire is adjacent and parallel to the hole to be drilled through the pipe 32. The anchoring provided by the cup 36, the ankle strap 42 and the K-wire 44 stably and correctly position the pipe 32 for guiding a coring reamer or a drill. The tunnels may thus be cored without a guide pin in the core. The tibial tunnel is reamed first and the core removed. The knee is flexed or extended a variable amount in order to properly position the femoral tunnel. A longer coring reamer is then directed through the tibial tunnel for drilling in and through the femur. The bone core from the femur is removed. Standard deburring and debridement procedures are followed.

Figure 8:
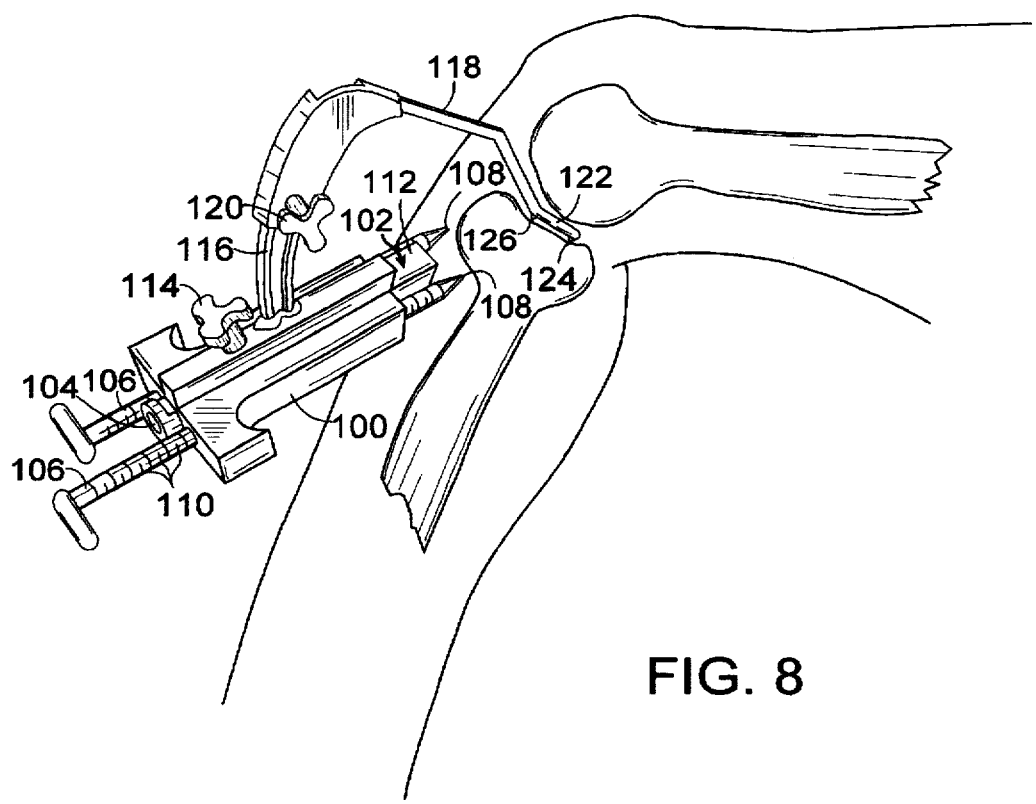
FIG. 8 is an isometric view of a tibial guide for use with the present invention against a knee.

A presently preferred embodiment of the tibial guide is shown in FIG. 8. Rigid stabilization of the guide against the knee is accomplished without the need for an ankle strap. A base 100 has a longitudinal open passage for receiving a guide tube 102. The guide tube 102 has a cylindrical tunnel 104 longitudinally therethrough. Guide tubes may be made with different diameter cylindrical tunnels to accommodate reamers or drills of corresponding diameter. The cylindrical tunnel 104 must be tight enough around the reamer to accurately guide it but wide enough to permit the reamer to rotate therein. On either side of the cylindrical tunnel, anchoring pins 106 or outriggers may be inserted. The two anchoring pins 106 provide two points of stability for the base against the tibia. The anchoring pins 106 have pointed ends 108 that can pierce skin. Therefore, it is not necessary to insert the pins through an incision, and they can be used to poke their own holes. The anchoring pins 106 securely engage the anterior margin of the tibia. The anchoring pins are notched along their length on one side. Inside the base 100, the notches 110 engage internal ridges to act like a ratchet. As the anchoring pins 106 are extended out from the base the notches click against the ridges. The anchoring pins 106 are prevented from retracting by the notches and ridges. To remove an anchoring pin from a patient, the handle on the proximal end of the anchoring pin is turned 180° to disengage the notches from the ridges. Then the anchoring pin can move freely longitudinally in either direction. The handle of the anchoring pin may advantageously be arranged as a flag which points horizontally outward from the base when the notches are engaged and points inward toward the other anchoring pin when the notches are disengaged. The adjustability of the anchoring pins accommodates the variation in leg size encountered from patient to patient.

Once the anchoring pins 106 have been adjusted, the guide tube 102 can also be reciprocally adjusted. The top outer surface 112 of the guide tube preferably has a flat portion for engagement with a set screw. A knob 114 on top of the base can be turned to tighten or release the screw from the guide tube. With the screw released, the guide tube 102 is pushed up against the tibia to thereby provide three points of engagement near the entrance of the tunnel to be drilled.

A curved track 116 is securely attached vertically to the base 100. A positioning arm 118 is adjustably mountable on the curved track. A screw handle 120 on the positioning arm is used to tighten the arm 118 against the vertical track 116. The positioning arm 118 can be slid along the track 116 to assume a range of positions. The range alters the angle made between an axis of the cylindrical tunnel of the guide tube and a seating portion 122 at the distal end of the positioning arm within a range of between about 45°–50° and 80°. By providing a sufficiently large minimum angle of between 45° and 50°, the tibial guide ensures that the tibial tunnel is not drilled at too shallow an angle.

The seating portion 122 of the positioning arm at the distal end of the arm is provided with two anchoring spikes 124 and 126. The spikes project from the end of the positioning arm for insertion into the top of the tibia. The spikes precisely define the exit end of the tunnel to be drilled through the tibia, and thus permit the surgeon to know on inspection and control the tunnel's location. Therefore, it is desirable to place the spikes so that the anatomic center of the anterior cruciate ligament is located midway therebetween. The spikes are sharp so that they may dig into the tibia. A first spike 124 extends from near the end of the positioning arm. The seating portion 122 of the positioning arm is curved between the first spike 124 and a second spike 126. The curve defines and identifies an open region to permit clearance for a coring reamer used in operation to drill a hole through the bone. Thus, the positioning arm does not interfere with the drilling process. Moreover, the seating portion 122 partially encircles the tunnel to be drilled and the spikes are inserted on opposite sides of the tunnel to be drilled. The two spikes on the positioning arm and the two anchoring pins through the base provide four points of stabilization which make for a completely rigid attachment between the tibial guide and the tibia. The attachment is advantageously rigid in three dimensions.

The seating portion 122 may be secured with a peg instead of the anchoring spikes. The peg may be located on the distal end of the seating portion for insertion over the top of the ridge where the posterior cruciate ligament inserts. The seating portion fits snugly up against the anterior aspect of the posterior cruciate ligament with the peg depending down beyond the ridge. The arrangement is oriented to drill the tunnel as previously described.

Figure 10:
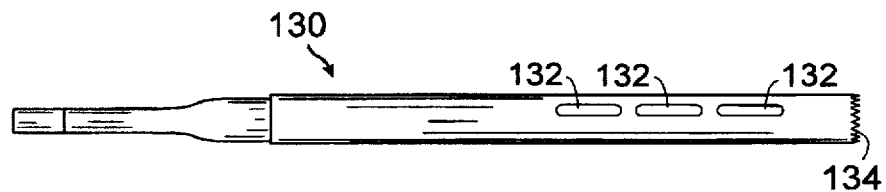
FIG. 10 is an isometric view of a coring reamer for use with the present invention.

With the tibial guide rigidly attached to the tibia, it is a relatively simple matter to insert the coring reamer through the cylindrical tunnel and drill an accurate tunnel. Advantageously, the bone core is not exposed to the damage ordinarily accompanying the use of a guide wire. However, without the hole through the bone caused by a guide wire, the bone core plugs up the coring reamer with almost fluid-tight engagement. Pulling the bone core out from a conventional coring reamer would be difficult because they are generally solid cylinders. Air or other fluid cannot get in behind the bone core so that pulling on the bore core tends to create a vacuum behind the bone core. The suction of the vacuum pulls the bone core into the coring reamer making it difficult to remove. A coring reamer 130 is used that is slotted to permit air or fluid in behind the bone core as shown in FIG. 10. The slots or openings 132 are a greater distance from the cutting edge 134 of the reamer than the length of a bone core to be drilled out. The cutting edge 134 includes a series of teeth alternately bent in toward the axis of the reamer and bent out away from the reamer. A rod can be inserted through a slot or opening behind the bone core to easily push the bone core out from the reamer. A bone core obtained using the tibial guide and coring reamer 130 may be used and replaced in the body as a part of the graft used for the reconstruction.

Figure 4A:
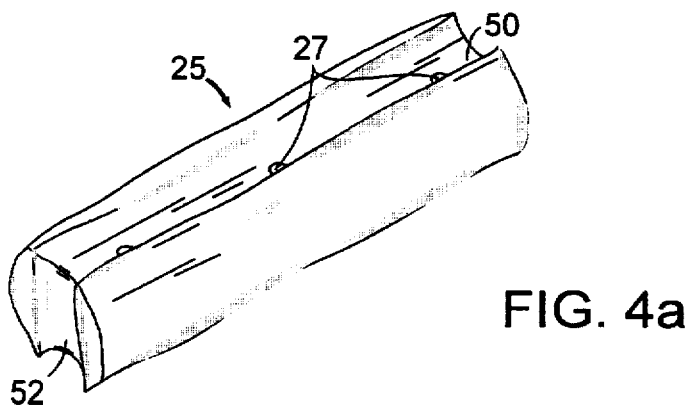
FIG. 4a is an isometric view of a bone plug made with the invention.
Figure 4B:
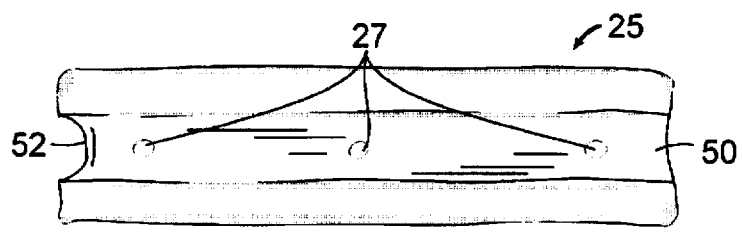

If cores have been drilled out from the bone tunnels they may be used for the bone plugs 25 otherwise, donor bone, namely allograft bone, can be used to make the bone plugs. Referring now to FIGS. 4a and 4b, whatever bone plug 25 is used, two longitudinal substantially parallel grooves 50 are drilled on opposite sides of each bone plug. The grooves provide a recess in which the semitendinosus tendon 20 and gracilis 21 can be seated. A notch 52 may also be drilled, if desired, across one end of the bone plug so that the tendon can be wrapped alongside and around the end of the bone plug, without protruding excessively from the plug. The notch 52 is not required because the bone tunnel is open at each end providing no restriction on the tendon projecting above the end of the graft. It is also advantageous to provide suture holes 27 through the bone plug for attaching the tendon to the plug. The suture holes 27 are drilled into the grooves radially through the bone plug and from one of the substantially parallel grooves 50 to the other.

Figure 7A:
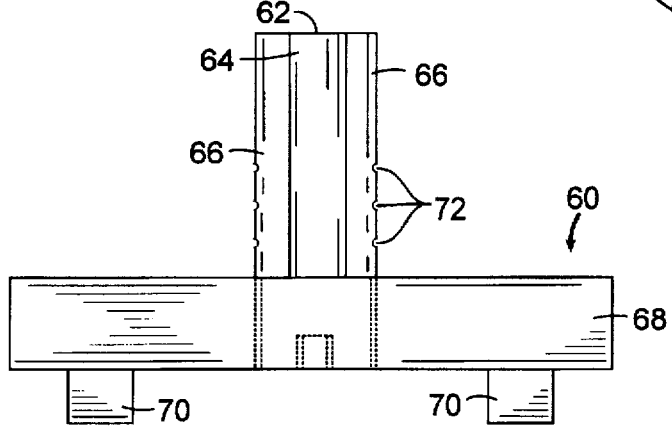
FIG. 7a is a side view of a bone block drill guide.
Figure 7B:
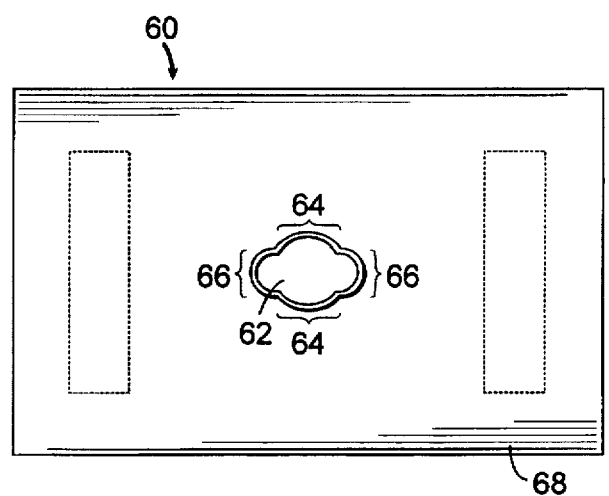

In order to easily and efficiently form a bone core into the desired bone plug for a composite graft, a bone block drill guide 60 of an embodiment of the invention as shown in FIGS. 7a and 7b may be used. The drill guide 60 features a central substantially cylindrical column 62. The central column 62 includes a pair of opposing curved walls 64 having a center of curvature substantially coincident with the center axis through the column 62. The curved walls 64 are shaped so as to hold a bone core parallel with the axis of the column and substantially centered within the column. A second pair of opposing curved walls are arranged at 180° to each other with respect to the central column formed by the curved walls 64. This second pair of walls are the drill guide walls 66. The drill guide walls 66 form two parallel columns on opposite sides of the central column. The drill guide walls 66 have a shorter radius of curvature than the first pair of opposing curved walls 64. In accordance with a presently preferred embodiment, the inner diameter of the drill guide walls 66 is 6 mm whereas the inner diameter of the first pair of opposing walls 64 is 11 mm. The central column 62 is mounted over a base 68. A bone core standing in the central column 62 rests on the base 68. The base 68 is provided with holes therethrough in alignment with the open circular cylinder formed within the drill guide walls 66. The base 68 may also include legs 70 for supporting the drill guide over a table. For drilling suture holes through the bone block, holes 72 are arranged horizontally through the drill guide walls 66. Three holes 72 are preferably aligned in a line.

The substantially parallel grooves 50 are drilled by inserting the bone core or allograft into the center chamber of the column 62 formed by the opposing curved walls 64. A drill is directed in the column 62 along each of the drill guide walls 66 in succession. Thus, parallel grooves 50 are formed on opposite sides of the bone core. The drill may be equipped with a stop to prevent the drill from being directed too far down through the column where it may contact the table beneath. A drill bit inserted through the holes 72 can be easily directed through the center of a groove drilled along the bone core. The suture holes drilled through guide holes 72 preferably extend from one groove to the opposite groove in the bone block.

Figure 5:
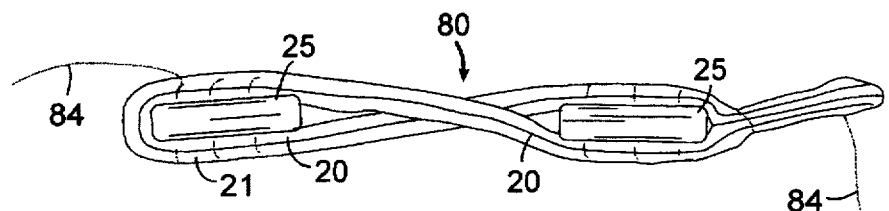
FIG. 5 is a side view of a bone-tendon-bone composite graft made with the present invention.

The semitendinosus tendon 20 and/or gracilis 21 is extended between both of the bone plugs 25. The tendons are seated inside the two substantially parallel grooves 50 and about an end of each bone plug. The tendons are preferably sutured to themselves to form a double loop as shown in FIG. 5. Sutures are also used through the suture holes to attach the tendon to each of the bone plugs. The tendon strands may be straight or twisted between the bone plugs. Twisting will shorten the length of the graft. A ligament replacement may include both the semitendinosus tendon and the gracilis. As such four strands will connect the two bone plugs. Other embodiments may use one or the other of the semitendinosus tendon and gracilis. Still further embodiments may substitute or combine man made or artificial fibers or human tissue for the tendons for use as the ligament replacement.

Figure 12:
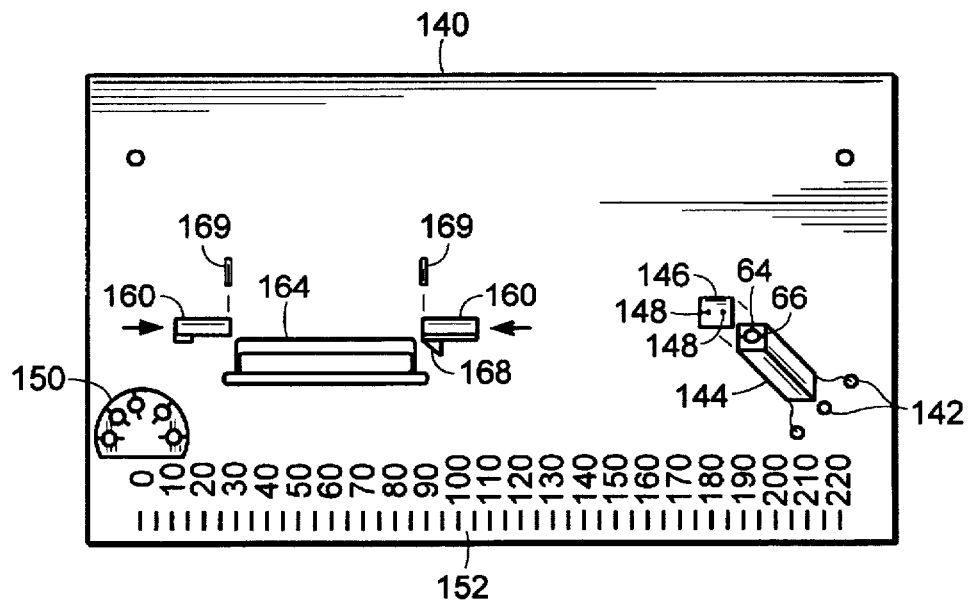
FIG. 12 is an illustration of a graft preparation table of the present invention.

A still easier method of making the composite graft can be accomplished by use of the graft preparation table 140 of a presently preferred embodiment of the invention as shown in FIG. 12. The table 140 includes a series of holes 142 in which a bone block drill guide such as column 62 having matching pegs along its bottom may be supported. FIG. 12 illustrates a bone block guide 144 having drill guided walls 64, 66 as described above with respect to drill guide 60. A drill guide cap 146 is provided with two holes 148. Each hole aligns with one of the two parallel columns on opposite sides of the central column through bone block guide 144. The cap 146 and bone block drill guide 144 have mating alignment pins and holes for guaranteeing the correct alignment. The cap 146 may be chained to the bone block drill guide to make sure it is not lost.

After inserting a bone block into the bone block drill guide 144, the cap 146 is placed into alignment over the guide. The longitudinal grooves are drilled by inserting the drill bit down through the holes 148 in the cap. After drilling the grooves, the cap is removed. The bone block can be removed by lifting the bone block drill guide 144 off the graft preparation table 140 and pushing the bone block out of the guide.

The graft preparation table 140 may be additionally provided with sizing tubes 150 of different diameters. The sizing tubes are useful in determining the diameter of a bone block. A linear scale 152 may also be included for permitting length measurements.

Figure 13A:
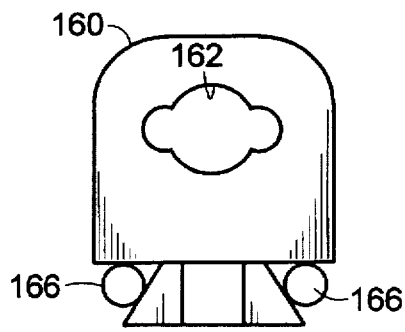
FIG. 13A is an end view of a suture block for use on the graft preparation table of FIG. 12.

The graft is completed by attaching the semitendinosus tendon and gracilis in a loop about the bone blocks. Suture blocks 160 assist in this process. A suture block 160 as shown in FIG. 13A includes a tunnel 162 that has two channels opposite one another across the central hole. The channels accommodate the tendon and gracilis looped about the bone block. The suture block 160 rides on a track 164 on the graft preparation table. The track 164 is formed by two parallel rails 166. The suture block 160 includes a pair of grooves for holding the block against the rails and permitting the block to ride along the rail. A ratchet rod 168 is used to apply tension on the ligament replacement looped about the bone blocks. The suture blocks include a vertical hole for accepting a stop pin 169 for holding the bone block within its tunnel. The pin 169 prevents the block from being pulled out of the suture block when the graft is being tensioned.

One of the suture blocks 160 is fixed in position on the track. The other suture block 160 is fixed to the ratchet rod 168. The ratchet rod 168 has a series of grooves spaced along its length. The ratchet rod 168 travels in a tube parallel to the track. The tube includes ridges along its inner circumference which engage walls of the grooves on the ratchet rod 168. The ridges and grooves prevent the ratchet rod 168 from moving the attached suture block toward the other suture block. The tension on the semitendinosus tendon and gracilis loop can be increased by pulling out the ratchet rod 168 to achieve the desired tension. In order to release the tension, the ratchet rod 168 is rotated to disengage the grooves from the ridges. The rod may then be pushed back into its tube.

Figure 13B:
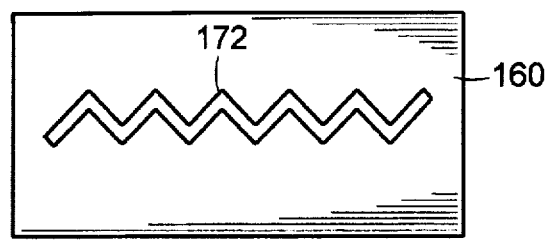
FIG. 13B is a side view of the suture block of FIG. 13A.

Referring now to FIG. 13B, the sides of each suture block include a suturing groove 172. The groove 172 of the current embodiment is an opening through the side of the suture block in the shape of a zig-zag. The same groove is on opposite sides of each suture block. Thus, a needle can be inserted through one side and out through the opposite side pulling the suture through the ligament replacement and the bone block. Suturing secures the loop of ligament replacement to the bone blocks.

Figure 14:
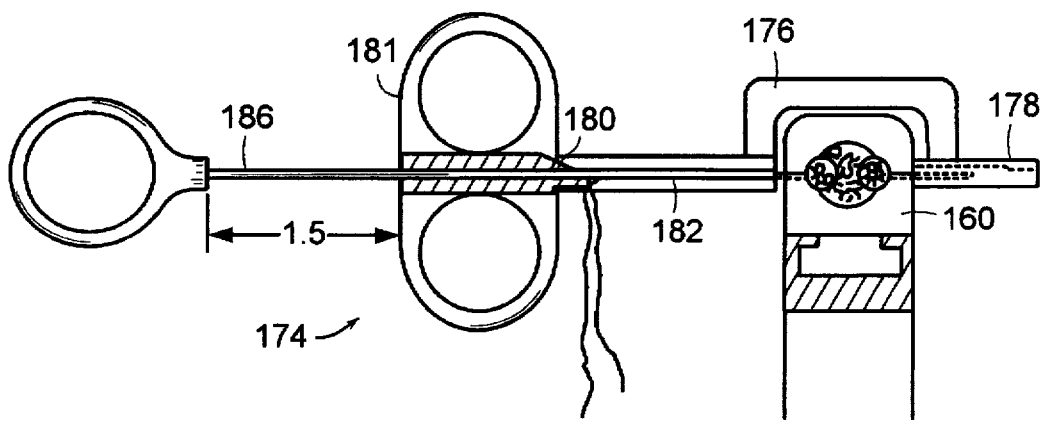
FIG. 14 is a side view of a needle pusher for use with the suture block of FIGS. 13A and 13B.
Figure 15:
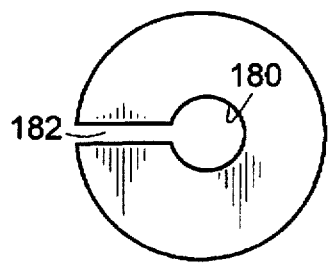
FIG. 15 is an end view of the insertion tunnel of the needle pusher of FIG. 14.
Figure 16:
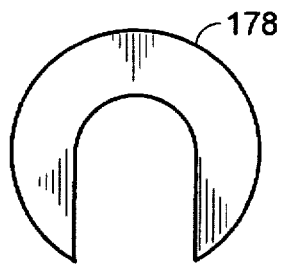
FIG. 16 is an end view of the receiving thimble of the needle pusher of FIG. 14.

Suturing may be facilitated by use of a needle pusher 174. Referring to FIGS. 14, 15 and 16, the needle pusher 174 helps minimize risk of inadvertently puncturing a finger with the needle used for suturing. The needle pusher 174 also helps apply greater force to push a needle through the bone block. The needle pusher 174 includes a frame 176 which fits over the suture block 160. The frame 176 includes a protected tip or thimble 178 for receiving a needle end and an insertion tunnel 180. A handle 181 is provided about the insertion tunnel 180. An open slot 182 in the insertion tunnel permits a suture to hang out of the tunnel from the needle. The slot 182 is large enough for the suture but too small for the needle to fit through. The thimble 178 is an open sleeve. It is open along one side so that the needle pusher 174 can be lifted off away from the needle. A push rod 186 is provided which fits into the insertion tunnel 180.

Suturing is performed with a needle, a Keith needle for example, having a suture attached. Suturing may preferably be performed with the suture blocks held apart on the track 164 to maintain a desired tension in the ligament replacement. The back of the needle is inserted into the insertion tunnel 180 at the end of the tunnel that will be placed against the suture block 160. The suture attached to the needle fits through the suture slot 182. By pulling on the suture, the needle can be pulled completely back into the insertion tunnel 180. The needle pusher 174 is placed over the suture block 160. The push rod 186 is inserted into the insertion tunnel 180. By pushing on push rod 186, the needle is pushed through the ligament replacement loop and bone block. When the push rod 186 has been fully inserted, the needle has pierced the graft and has an end sticking out into the thimble 178. The needle pusher 174 is lifted off from the suture block 160. A grasper may be used to grasp the needle sticking out from the suture block and pulling the needle all the way out from the graft and the suture block. These steps may be repeated to push the needle back through the suture block in the opposite direction. Upon suturing both bone blocks, the tension between the blocks can be released and the composite graft removed. The graft is now ready for use in the surgical reconstruction.

Figure 3A:
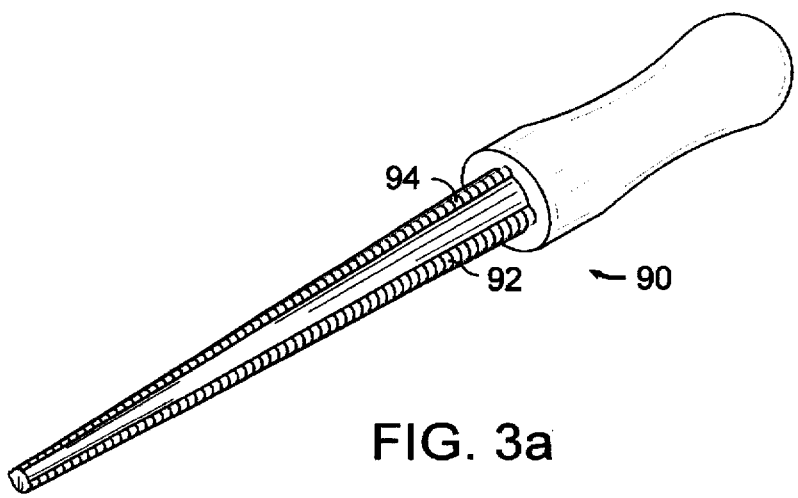
FIG. 3a is an isometric view of a tri-flange broach for use with the present invention.
Figure 3B:
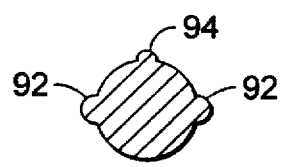
Figure 11:
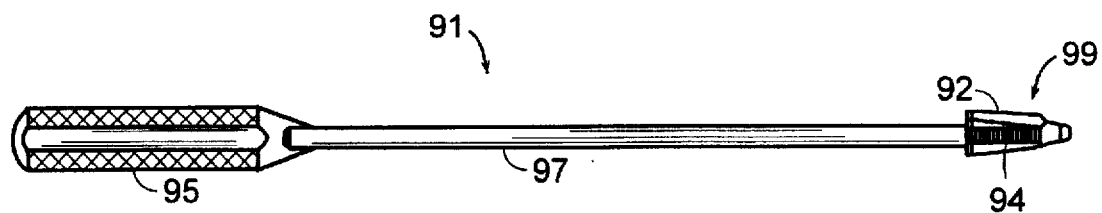
FIG. 11 is a plan view of a presently preferred embodiment of a tri-flange broach.

In affixing the composite graft 80 within a bone tunnel, contact between a screw 82 and the tendon should be avoided so as not to cut or tear the tendon. To better insure that the screw is out of contact with the tendon, an interference screw should be driven along the bone portion of the graft between the graft and the bone tunnel wall. A tri-flange broach 90 of the present invention is recommended for use prior to fixation of the graft. As shown in FIGS. 3a and 3b, the tri-flange broach 90 has three longitudinal cutting lobes for use in cutting three channels into each of the bone tunnels. A presently preferred embodiment of the tri-flange broach 91 is shown in FIG. 11. Broach 91 includes a handle 95, a shaft 97 and a cutting end 99. Reciprocating movement of the tri-flange broach 91 in and out of the bone tunnels 16 serves to file away the tunnel walls to form the desired channels. Two of the longitudinal lobes 92 are 180° apart on the broach. These longitudinal lobes 92 are used to form channels for accommodating the semitendinosus tendons 20 and gracilis 21 seated in the parallel grooves of the bone graft. When the gracilis 21 is attached along and on top of the semitendinosus tendon 20, the channels are required to provide room for the graft to fit within the tunnel.

Figure 6:
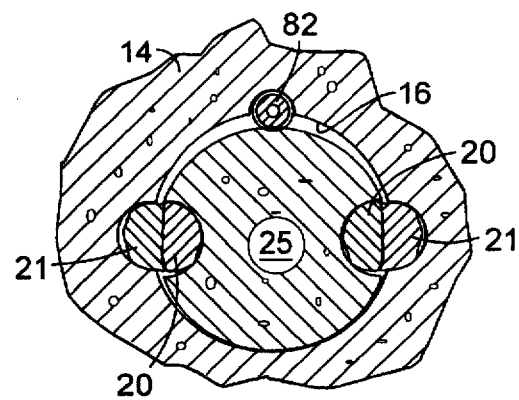
FIG. 6 is a cross-sectional view of FIG. 1 taken along lines 6—6.

The third longitudinal lobe 94 is located parallel to and equidistant from the two opposed lobes. Looking at the end of the broach as in FIG. 3b, the cross-section of the cutting portions of broach 90 and 91 appear the same. The third lobe 94 is preferably 90° to each of the other two lobes. The third cutting lobe 94 of the broach advantageously files away a channel along which an interference screw is driven as shown in FIG. 6. The channel helps to maintain the screw straight adjacent the bone portion of the graft. In the presently preferred embodiment, the third lobe 94 and the other two lobes 92 each project 2 mm. from a core. The core expands from its distal end to its widest portion. At its widest, the core diameter is less than the diameter of the tunnel in which the broach will be used. At its distal end, the core is about 4 mm. smaller in diameter than at its widest portion. The tip of the broach 91 has a bullet nose shape.

After the channels have been filed in the bone tunnels, the sutures 84 hanging from one end of the composite graft are attached to a needle, a passer or other conventional graft placement tool. The passer is inserted through tibial and femoral bone tunnels and out through the skin on the posterior side of the knee. The passer is removed leaving the suture hanging from the posterior end of the graft and a suture at the other end of the graft hanging out through the tibial incision. The sutures may be pulled on to properly tension and locate the graft within the bone tunnels. Alternatively, the graft may be positioned within the bone tunnels using a pushing device instead of a suture pulling the graft into position.

Fixation of the graft can be accomplished with a headless cannulated interference screw. The cannulated interference screw can be carried by a guide wire extending from the tip of an angled driver. The guide wire is preferably a springy wire made of a material such as Nitinol™. The wire extends about 2 centimeters past the end of a screw carried by the driver. For securing the interference screw in the femoral tunnel, the angled or flexible driver and screw are preferably inserted through the anteromedial portal. An angled driver and use thereof is described in U.S. Pat. No. 5,391,170, the entire disclosure of which has been incorporated by reference herein. A flexible slide may be used to provide a track to follow from the anteromedial portal to the channel in the femoral tunnel for the interference screw. The insertion of a flexible slide simplifies the guidance of the interference screw into the channel of the femoral tunnel. Once the screw is properly positioned in the tunnel, the driver can initiate screwing and the slide can be removed. The oppositely located channels in the femoral tunnel hold the semitendinosus tendon in position away from the interference screw as it is screwed between the bone portion of the graft and the channel of the bone tunnel. Upon fixation of the interference screw in the femoral tunnel, the angled driver is removed.

The proper tension is then applied to the graft by pulling on the suture hanging out from the tibial incision. A driver and a headless cannulated interference screw are then inserted through the tibial incision for driving the screw along the channel formed in the tibial tunnel. The sutures are cut and the incisions are closed. The reconstructed knee upon fixation of the graft appears as in FIG. 1.

While this operation has been discussed in terms of using autogenous bone cores, alternative sources of bone plugs may be substituted. Allografts, in which donor bone is freeze-dried or fresh frozen for preservation, are one alternative. The freeze drying process kills cells in the bone and may reduce the risk of transmission of infection. Another alternative bone plug is the use of synthetic graft material. With any of these alternatives, the bone plugs may be shaped to appear as described above for the autogenous graft. With the allograft and the synthetic graft, the coring reamer is no longer required and an ordinary drill may be used instead for drilling the bone tunnels.

The surgical technique of the present invention advantageously makes use of the fact that the semitendinosus and gracilis has less morbidity associated with harvesting than does the patellar tendon. It is further advantageous to use a coring reamer and a bone block drill guide of the invention to remove the bone cores from the bone tunnels in the tibia and femur and shape them to accommodate the semitendinosus tendon. The tri-flange broach provides the still further advantage of maintaining alignment of the graft and interference screws in the bone tunnel so that the screw is directed adjacent only the bone portion of the graft.

I claim:

1. A bone block drill guide comprising:
   a base;
   a central column supported by said base and sized to accommodate a longitudinally inserted bone plug; and
   first and second parallel cylindrical columns intersecting opposite sides of said central column equidistant from the center of said central column, said first and second cylindrical columns each having a center, the centers of said central column and said first and second columns all being aligned.

2. The bone block drill guide of claim 1 further comprising a cap having two holes for fitting a drill therethrough and means for mounting said cap over said central column and said first and second columns so that the two holes align with the centers of said first and second columns.

3. A bone block drill guide comprising:
   a body having a central tunnel for receiving a bone block and first and second parallel tunnels intersecting opposite sides of the central tunnel and being parallel to the central tunnel; and
   a cap having two holes for fitting a drill therethrough and means for mounting said cap over said body so that the two holes align with the centers of said first and second tunnels.

4. A method for making a graft comprising:
   inserting a bone block into a central tunnel of a body, said body having first and second parallel tunnels intersecting opposite sides of the central tunnel and being parallel to the central tunnel;

inserting a drill into one of said first and second tunnels;

drilling a first groove in said bone block;

inserting a drill into the other of said first and second tunnels;

drilling a second groove in said bone block opposite from and parallel to the first groove; and attaching a ligament replacement to said bone block.

5. The method of claim 4 further comprising looping a ligament replacement about said bone block along the first and second grooves.

6. The method of claim 5 further comprising tensioning the ligament replacement.

7. The method of claim 6 wherein said step of attaching comprises suturing the ligament replacement while tensioned to the bone block.

8. A suturing station comprising:

a tensioning track;

a pair of suture blocks separated along said tensioning track, each suture block having a chamber for accommodating a bone block and suturing openings on opposite sides of the suture block, the suturing openings of the opposite sides being aligned with one another with the chamber therebetween; and means for holding the suture blocks an adjustable distance apart from one another along said tensioning track.

9. The suturing station of claim 8 wherein the chamber in each suture block has a central tunnel and first and second parallel tunnels intersecting opposite sides of the central tunnel and being parallel to the central tunnel.

10. The suturing station of claim 9 wherein the suturing openings of each suture block are aligned so that a needle inserted into the suture block through one of the suturing openings can be extended through each of the central tunnel, the first tunnel and the second tunnel and into the suturing opening on the opposite side.

11. The suturing station of claim 8 wherein said means for holding comprises a ratchet rod having a series of grooves for adjustably engaging ridges that are fixed in position relative to said tensioning track.

12. The suturing station of claim 11 wherein the ratchet rod is arrange with respect to the ridges so that axially rotating the ratchet rod can disengage the grooves from the ridges.

13. The suturing station of claim 8 wherein each suture block includes means for receiving a stop pin for holding a bone block within the chamber.

14. A method for making a graft comprising the steps of:

providing first and second bone plugs, each having on its outer surface two longitudinal substantially parallel grooves opposite one another on said each bone plug;

extending at least one ligament replacement between both of the first and second bone plugs along the two substantially parallel grooves in each bone plug;

holding the first and second bone plugs apart from one another to tension the at least one ligament replacement; and suturing the at least one ligament replacement to the first and second bone plugs while they are being held apart.

15. A method for making a graft comprising the steps of:

providing first and second bone plugs, each having two longitudinal substantially parallel grooves opposite one another on said each bone plug;

extending at least one ligament replacement between both of the first and second bone plugs along the two substantially parallel grooves in each bone plug;

holding the first and second bone plugs apart from one another to tension the at least one ligament replacement;

suturing the at least one ligament replacement to the first and second bone plugs while they are being held apart; and inserting the first and second bone plugs along with the at least one ligament replacement each into a suture block before said step of holding, each suture block having a chamber for accommodating one of the bone plugs and the at least one ligament replacement and suturing openings on opposite sides of the suture block, the suturing openings on opposite sides being aligned with one another with the chamber therebetween.

16. The method of claim 15 further comprising inserting a stop pin into each of the suture blocks before the step of holding so as to keep each bone plug within its respective suture block.

17. The method of claim 15 wherein said step of suturing includes inserting a needle carrying a suture into one of the suturing openings in one of the suture blocks through the at least one ligament replacement and the bone plug and out through the other of the suturing openings in the one of the suture blocks.

18. A graft preparation table comprising:

a base;

a body, mounted on said base, having a central tunnel for receiving a bone block and first and second parallel tunnels intersecting opposite sides of the central tunnel and being parallel to the central tunnel;

a tensioning track mounted on said base;

a pair of suture blocks separated along said tensioning track, each suture block having a chamber for accommodating a bone block and suturing openings on opposite sides of the suture block, the suturing openings of the opposite sides being aligned with one another with the chamber therebetween; and means for holding the suture blocks an adjustable distance apart from one another along said tensioning track.

19. The graft preparation table of claim 18 wherein said means for holding comprises a ratchet rod having a series of grooves for adjustably engaging ridges that are fixed in position.

20. The graft preparation table of claim 18 further comprising a plurality of sizing tunnels mounted on said base.

* * * * *